United States Patent [19]

Imai et al.

[11] Patent Number: 5,198,587
[45] Date of Patent: Mar. 30, 1993

[54] PHENETHYLAMINE DERIVATIVES

[75] Inventors: Kazuo Imai; Kunihiro Niigata; Takashi Fujikura, all of Saitama; Shinichi Hashimoto, Matsudo; Toichi Takenaka, Tokyo; Kazuo Honda, Saitama, all of Japan

[73] Assignee: Yamanouchi Pharmaceutical Co., Ltd., Tokyo, Japan

[21] Appl. No.: 737,976

[22] Filed: Jul. 30, 1991

Related U.S. Application Data

[60] Division of Ser. No. 569,780, Aug. 21, 1990, Pat. No. 5,063,246, which is a continuation of Ser. No. 364,579, Jun. 9, 1989, abandoned, which is a continuation-in-part of Ser. No. 253,368, Sep. 30, 1988, abandoned, which is a continuation-in-part of Ser. No. 24,605, Mar. 11, 1987, abandoned, which is a continuation-in-part of Ser. No. 894,464, Jul. 31, 1986, abandoned, which is a continuation-in-part of Ser. No. 690,398, Jan. 9, 1985, abandoned, which is a continuation-in-part of Ser. No. 517,734, Jul. 28, 1983, abandoned, which is a continuation-in-part of Ser. No. 385,782, Jul. 22, 1981, abandoned.

[30] Foreign Application Priority Data

Jul. 29, 1980 [JP] Japan .................................. 55-104175
Jun. 15, 1981 [JP] Japan .................................. 56-92010

[51] Int. Cl.$^5$ .................................. C07C 217/60
[52] U.S. Cl. .................................. 564/374; 558/61; 564/353; 564/354; 564/363; 564/364; 564/365; 564/381; 564/382

[58] Field of Search ............... 564/353, 354, 363, 364, 564/369, 374, 381, 382; 558/61

[56] References Cited

U.S. PATENT DOCUMENTS

| | | | |
|---|---|---|---|
| 3,954,871 | 5/1976 | Buu-Hoi et al. | 564/363 |
| 4,048,229 | 9/1977 | Colella et al. | 564/344 |
| 5,063,246 | 11/1991 | Imai et al. | 514/517 |

Primary Examiner—Richard L. Raymond
Attorney, Agent, or Firm—Burgess, Ryan & Wayne

[57] ABSTRACT

Phenethylamine derivatives shown by the general formula

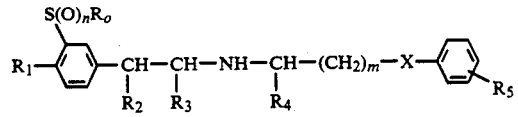

wherein $R_o$ represents a lower alkyl group; $R_1$ represents a lower alkyl group or a lower alkoxy group; $R_2$ represents hydrogen atom or a hydroxyl group; $R_3$ and $R_4$ each represents hydrogen atom or a lower alkyl group; $R_5$ represents hydrogen atom or a lower alkoxy group; X represents oxygen atom or a methylene group; m is an integer of 1-3; and n is an integer of 0-2 and the acid addition salts thereof.

These compounds exhibit a strong α-adrenergic blocking action and are useful as an antihypertensive agent.

3 Claims, No Drawings

PHENETHYLAMINE DERIVATIVES

This is a division, of application Ser. No. 569,780, filed Aug. 21, 1990, now U.S. Pat. No. 5,063,246, which is a continuation of Ser. No. 364,579, Jun. 9, 1989, abandoned, which is a continuation-in-part of Ser. No. 253,368, Sep. 30, 1988, abandoned, which is a continuation-in-part of Ser. No. 24,605, Mar. 11, 1987, abandoned, which is a continuation-in-part of Ser. No. 894,464, Jul. 31, 1986, abandoned, which is a continuation-in-part of Ser. No. 690,398, Jan. 9, 1985, abandoned, which is a continuation-in-part of Ser. No. 517,734, Jul. 28, 1983, abandoned, which is a continuation-in-part of Ser. No. 385,782, Jul. 22, 1981, abandoned.

BACKGROUND OF THE INVENTION

1. Field of the Invention

This invention relates to novel phenethylamine derivatives and the acid addition salts thereof, and more particularly to novel phenethylamine derivatives and the acid addition salts thereof exhibiting a strong α-adrenergic blocking action and useful as an antihypertensive agent.

2. Description of the Prior Art

U.K. Pat. No. 1,321,701 discloses a series of compounds represented by the following formula

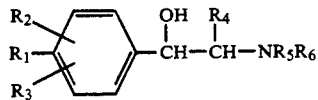

wherein $R_1$ is RS—, RSO— or $RSO_2$— (wherein R is an alkyl of $C_1$-$C_{10}$); $R_2$ and $R_3$ each is hydrogen, an alkyl of $C_1$-$C_3$, an alkoxy of $C_1$-$C_4$, or an alkylthio of $C_1$-$C_4$; $R_4$ represents hydrogen or an alkyl of $C_1$-$C_4$; and $R_5$ and $R_6$ each is an alkyl of $C_1$-$C_{16}$ which may a substituted by a phenyl group or a substituted phenyl group and states that these compounds exhibit a β-adrenergic blocking action, a peripheral vasodilating effect, an antiarrhythmic effect and a hypotensitive effect.

Belgian Pat. No. 856,055 discloses a series of compounds shown by the formula

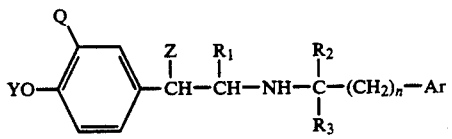

wherein Z is OH or H; $R_1$, $R_2$ and $R_3$ each is H or a lower alkyl group; n is 1-3; Ar is a phenyl group which may be substituted by 1 to 3 halogen atoms, lower alkyl groups, lower alkoxy groups or OHs; Q is lower alkyl-$S(O)_m$ (m is 0, 1, or 2); and Y is H, a lower alkanoyl group, an aroyl group, a benzenesulfonyl group, or a toluenesulfonyl group and states that these compounds exhibit a β-adrenergic blocking activity, a vasodilating activity, an antiarrhythmic effect and a hypotensive effect.

SUMMARY OF THE INVENTION

An object of this invention is to provide pharmacologically useful compounds which possess a hypotensive activity based on an α-adrenergic blocking action and can be used as an antihypertensive agent.

Another object of this invention is to provide a process of producing the aforesaid pharmacologically useful compounds.

According to this invention, there are provided phenethylamine derivatives shown by formula I and the acid addition salts thereof

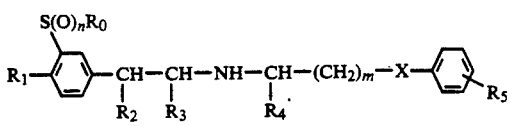

wherein $R_0$ represents a lower alkyl group; $R_1$ represents a lower alkyl group or a lower alkoxy group; $R_2$ represents hydrogen atom or a hydroxyl group; $R_3$ and $R_4$ each represents hydrogen atom or a lower alkyl group; $R_5$ represents a hydrogen atom or a lower alkoxy group; X represents oxygen atom or a methylene group; m represents an integer of 1-3; and n represents an integer of 0-2.

These compounds of this invention are useful as antihypertensive agents.

According to another embodiment of this invention, the compounds shown by the above-described formula I can be prepared as follows:

(1). A phenethylamine derivative shown by the general formula

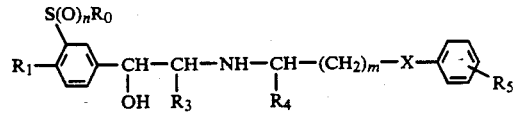

wherein $R_0$, $R_1$, $R_3$, $R_4$, $R_5$, X, m, and n have the same significance as defined in formula I can be obtained by reacting a halohydrin shown by the formula

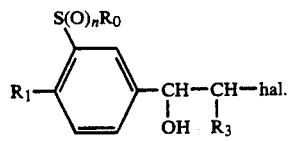

wherein hal represents a halogen atom and $R_0$, $R_1$, $R_3$ and n have the same significance as defined above or an epoxide shown by the formula

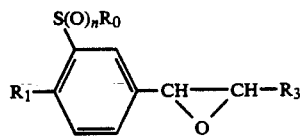

wherein $R_0$, $R_1$, $R_3$, and n have the same significance as defined above and an amine shown by the formula

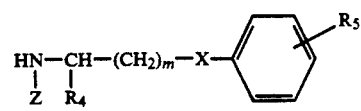

wherein Z represents a hydrogen atom or a benzyl group, and $R_4$, $R_5$, X, and m have the same significance as defined above and, when Z is a benzyl group, removing the group from the product.

(2). A phenethylamine derivative shown by the formula

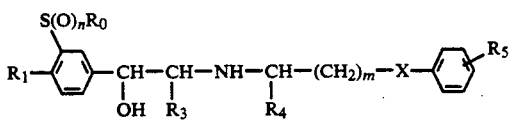

wherein $R_0$, $R_1$, $R_3$, $R_4$, $R_5$, X, m, and n have the same significance as in formula I can be prepared by reducing an aminoketone shown by the formula

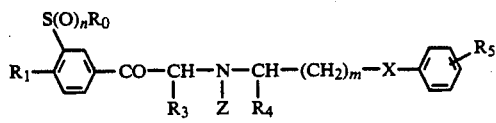

wherein $R_0$, $R_1$, $R_3$, $R_4$, $R_5$, X, m, and n have the same significance as defined in formula I and, when Z is a benzyl group, removing the group from the reduction product.

(3). A phenethylamine derivative shown by the formula

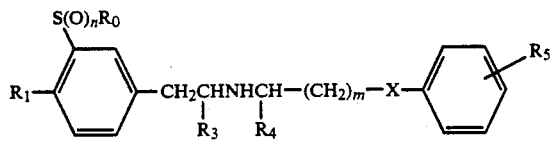

wherein $R_0$, $R_1$, $R_3$, $R_4$, $R_5$, X, m, and n have the same significance as defined in formula I can be prepared by condensing a ketone shown by the formula

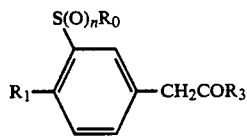

wherein $R_0$, $R_1$, $R_3$ and n have the same significance as above defined and an amine shown by the formula

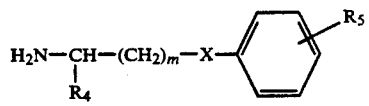

wherein $R_4$, $R_5$, X and m have the same significance as above defined, reducing the condensation product, and, when n is 0, further treating the product with an oxidizing agent.

DESCRIPTION OF THE PREFERRED EMBODIMENTS

Now, the term "lower" used in the above-described formulae means a straight or branched carbon chain having 1 to 5 carbon atoms. Therefore, for example, a lower alkyl group includes methyl group, ethyl group, propyl group, butyl group, pentyl group, isobutyl group, etc., and a lower alkoxy group includes methoxy group, ethoxy group, propoxy group, butoxy group, etc. Also, in the above-described formulae, the $R_5$ groups which are substituents of the benzene ring may be disposed at any position (i.e., ortho, meta; and para) to the side chain. Furthermore, since compound of formula [I] of this invention can form readily the salt thereof and contains asymmetric carbon atom(s), the compounds of this invention includes the salts thereof, the racemic compounds thereof, a mixture of the racemic compounds, and each optical active substance.

The compounds of formula [I] and the acid addition salts thereof provided by the present invention exhibit $\alpha$-adrenergic blocking actions. Therefore, they can be utilized for various treatments. For example, they can be used as useful agents for the treatment of hypertension, congestive heart failure, angina pectoris, lower urinary tract dysfunction, prostatic hypertrophy, pheochromocytoma and peripheral vascular disorders.

The pharmacological effects of the compounds of this invention were determined by the following experiments. The effects of the typical compounds of this invention were compared with those of 5-{1-hydroxy-2-[2-(2-methoxyphenoxy) ethylamino]ethyl}-2-methyl-benzenesulfonamide (referred to as "Compound A") which is one of the typical compounds disclosed in British Patent No. 2,006,772 and phentolamine.

A. $\alpha$-Adrenergic Blocking Action

The blood pressure was measured in the rats anesthetized with urethane and treated with pentolinium. The effects of the test samples (intravenous injection) to antagonize the hypertensive response to phenylephrine (10 µg/Kg i.v.) were measured and the results were shown in Table I.

B. Antihypertensive Effects in Spontaneously Hypertensive Rats

Oral administration:—The systolic blood pressure was measured indirectly by the tail cuff method using a programmed electrosphygmanometer (Nacro-Bio-Systems Inc., PE-300) on spontaneously hypertensive rats having the systolic blood pressure of higher than 150 mmHg, the results being shown in Table II.

TABLE I

| α-blocking activity | |
|---|---|
| compounds of this invention (Ex. No.) | α-blocking activity (rat) ED$_{50}$ (mg/kg) i.v. |
| 5 | 0.045 |
| 6 | 0.021 |
| 8 | 0.0019 |
| 12 | 0.00014 |
| known compounds: | |
| Compound A | 0.032 |
| phentolamine | 0.061 |

TABLE II

| antihypertensive effect | |
|---|---|
| compounds of this invention (Ex. No.) | change in systolic blood pressure (mm Hg) at stated dose (mg/kg)    dose P.O. |
| 5 | 30    −60 |
| 6 | 30    −64 |
| 8 | 30    −48 |
| 12 | 30    −58 |
| known compounds: | |
| Compound A | 30    −30 |
| phentolamine | 30    −53 |

The clinical administration of the compounds of this invention is usually intravenous injection or orally as the free base or an acid addition salt thereof (e.g., hydrochlorides, oxalates, sulfates, maleates, acetates, fumarates, lactates, citrates, etc.,). It is proper to administer about 0.01 mg per single dose of the compound several times per day in case of intravenous administration or about 1000 mg of the compound in two or three times per day in case of oral administration. The compounds of this invention may be formulated into ordinary dosage forms such as, for example, tablets, capsules, pills solutions, etc., and in these cases, the medicaments can be prepared by conventional method using usual medical excipients.

The compounds of this invention shown by formula [I] can be produced by the following processes. y amine of formula III in a non-solvent or an organic solvent. As the organic solvent used in the reaction, there are, for example, ethanol, toluene, methyl ethyl ketone, acetonitrile, tetrahydrofuran, dimethyl formamide, etc. Also, the reaction proceeds at room temperature to under heating but for promoting the reaction, the reaction is usually performed under heating or under refluxing.

Step 2: When Z is a benzyl group in compound $I_1'$ shown above, the benzyl group is removed by performing an ordinary catalytic hydrogenation using for example palladium carbon as a catalyst.

The isolation and purification of the reaction product of formula $I_1'$ or $I_1$ is performed by an ordinary opera-

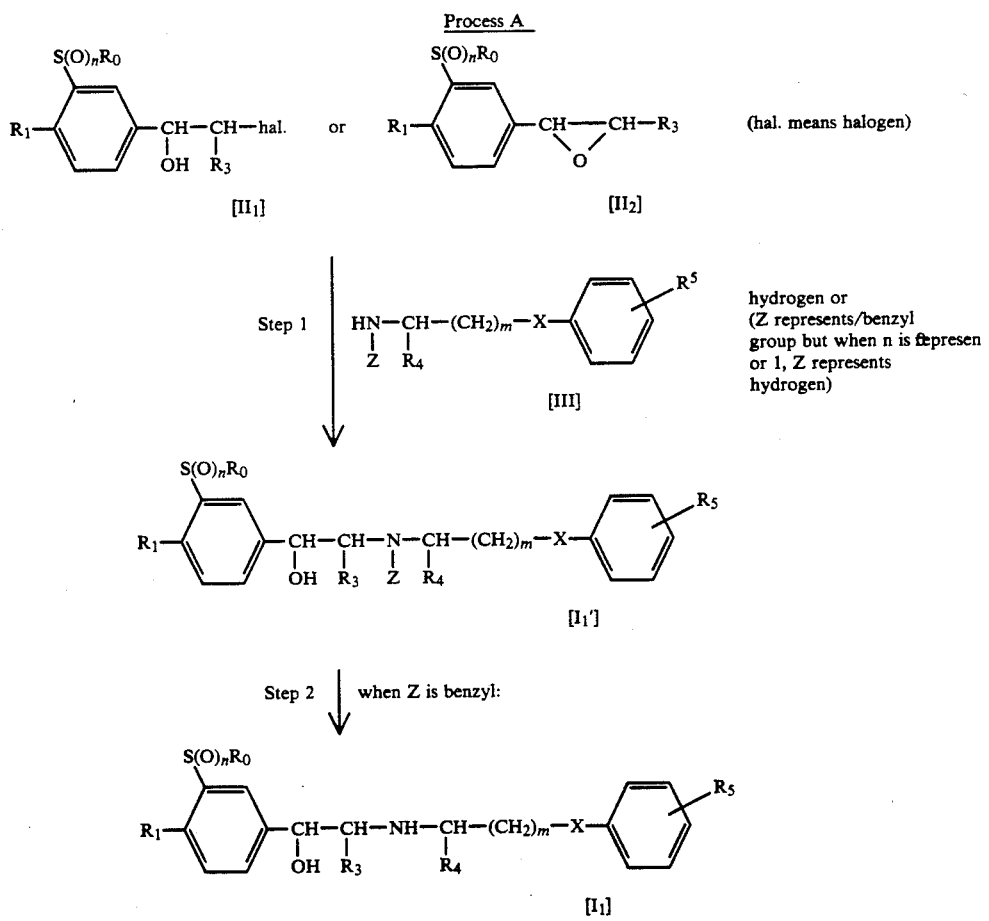

Step 1: Usually the process is performed by reacting the halohydrin of formula $II_1$ or the epoxide of formula $II_2$ and an equimolar amount to excessive amount of the tion such as filtration, extraction by solvent, column chromatography, recrystallization, etc.

Process B

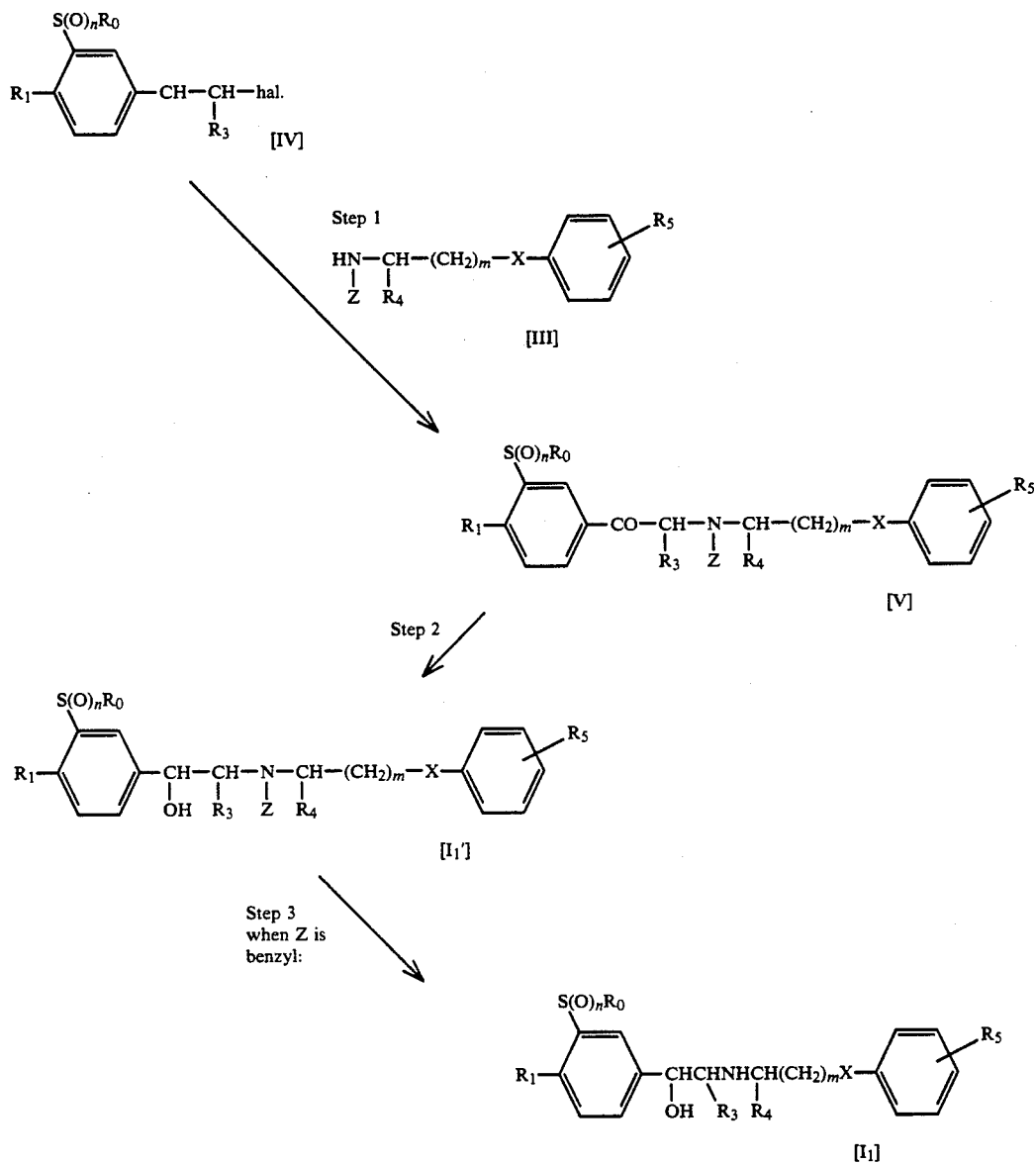

Step 1: This step can be practised under the reaction conditions as in Step 1 of Process A.

Step 2: This step can be performed in an organic solvent such as methanol, ethanol, toluene, acetonitrile, tetrahydrofuran, etc., under cooling or at room temperature using a complex metal hydride such as sodium borohydride, diborane, etc., and when the reduction is performed in the presence of a ordinary hydrogenation catalyst such as palladium carbon, etc., the removal of the benzyl group can be performed simultaneously.

Step 3: The step can be performed under the same reaction conditions as in Step 2 of Process A.

Process C

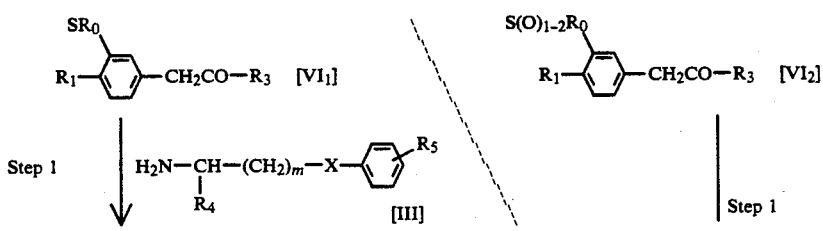

-continued
Process C

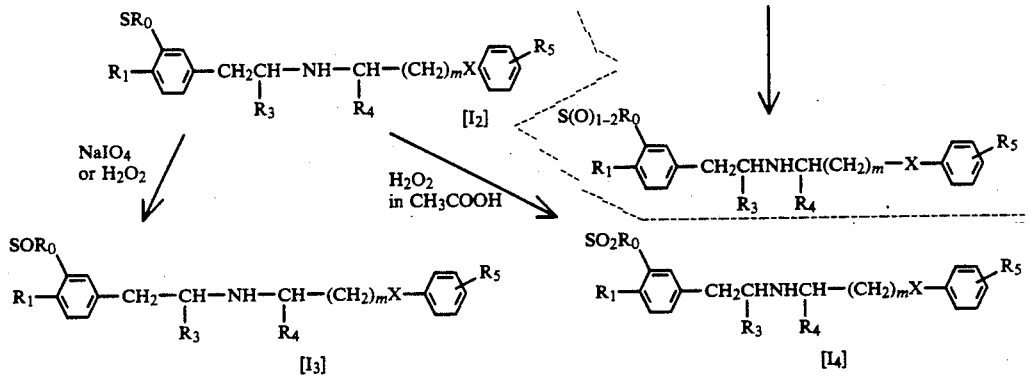

Step 1: A compound of formula I₂ is obtained by condensing the compound of formula VI and the compound of formula III in an organic solvent such as methanol, ethanol, toluene, acetonitrile, tetrahydrofuran, etc., and then reducing the condensation product in the presence of PtO₂ or a Raney nickel catalyst or with NaBH₄, etc.

Step 2: A sulfinyl compound of formula I₃ wherein n is 1 can be obtained by treating a compound of formula I₂ in an organic solvent such as methanol, ethanol, etc., using a proper oxidizing agent such as, for example, hydrogen peroxide aqueous solution (10–50%), sodium meta-periodate, etc. Also, a sulfonyl compound of formula I₄ wherein n is 2 can be obtained by treating together with an oxidizing agent (hydrogen peroxide aqueous solution, etc.,) in an acid solvent such as formic acid, acetic acid, etc.

Then, the production process of this invention will be further described in the following examples. In addition, the raw materials or intermediates used in the process of this invention include novel compounds and examples of the productions of these compounds are also shown in the following reference examples.

REFERENCE EXAMPLE 1

(a). Into a suspension of 300 g of stannous chloride di-hydrate in 1100 ml of glacial acetic acid, was introduced hydrogen chloride gas with stirring until the suspension became transparent and then a solution of 50 g of 3-chlorosulfonyl-4-methylacetophenone dissolved in 100 ml of glacial acetic acid was added thereto dropwise at 25°–30° C. After further stirring the mixture for one hour, 2,000 ml of water was added to the reaction mixture and the product was extracted with 1,000 ml of benzene. After washing the benzene extract with water, benzene was distilled off and the residue was distilled under reduced pressure to provide 37 g of 3-mercapto-4-methylacetophenone having a boiling point of 105°–115° C./2 mm Hg.

(b). A mixture of 31 g of 3-mercapto-4-methylacetophenone, 31 g of anhydrous potassium carbonate, 29 g of methyl iodide, and 360 ml of acetone was stirred for 3 hours at room temperature, the reaction mixture obtained was filtered, and the filtrate was evaporated to dryness. The residue formed was dissolved in benzene and after washing the solution obtained with water, benzene was distilled off. Then, the residue was distilled under reduced pressure to provide 29 g of 4-methyl-3-methylthioacetophenone having a boiling point of 96°–105° C./0.7 mm Hg.

(c). In 200 ml of carbon tetrachloride was dissolved 20 g of 4-methyl-3-methylthioacetophenone and then 18 g of bromine was added dropwise to the solution with stirring at room temperature. After the reaction was over, carbon tetrachloride was distilled off and the residue obtained was recrystallized from carbon tetrachloride to provide 18 g of 4'-methyl-3'-methylthio-2-bromoacetophenone having a melting point of 85°–86° C.

(d). To a mixture of 18 g of 4'-methyl-3'-methylthio-2-bromoacetophenone and 300 ml of methanol was gradually added 8 g of sodium borohydrate and thereafter the mixture was stirred for one hour at 40°–50° C. After distilling off methanol from the reaction mixture, 200 ml of water was added to the residue and the product was extracted with 300 ml of benzene. Then, benzene was distilled off and the residue formed was purified by a silica gel column chromatography (eluant:benzene) to provide 8.5 g of oily 4-methyl-3-methylthiostyrene oxide.

Nuclear magnetic resonance spectra (CDCl₃)

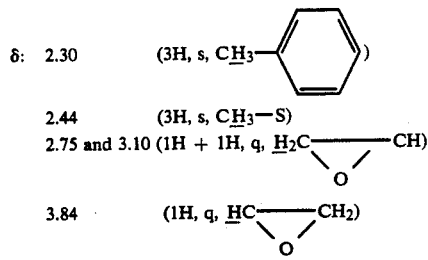

REFERENCE EXAMPLE 2

(a). To an aqueous solution of 400 g of sodium sulfite. -7H₂O dissolved in 615 ml of water was added 81 g of 3-chlorosulfonyl-4-methylacetophenone and the mixture was stirred for 30 minutes at 50°–55° C. After cooling, the reaction mixture was acidified by the addition of concentrated hydrochloric acid and extracted with 1,000 ml of ethyl acetate. The ethyl acetate layer obtained was washed with 500 ml of water, and after drying by anhydrous sodium sulfate, the solvent was distilled off to provide 50 g of a colorless caramel-like powder of 5-acetyl-2-methylbenzenesulfinic acid. The product was dissolved in 500 ml of 60% ethanol and after adding thereto 8 g of sodium hydroxide and 145 g of methyl iodide, the mixture was refluxed for 15 hours.

After the reaction was over, the solvent was distilled off and after adding water to the residue, the product was extracted with 1,000 ml of ethyl acetate. The ethyl acetate layer obtained was washed in succession with 300 ml of an aqueous 5% sodium thiosulfate solution, 300 ml of an aqueous 5% sodium hydroxide solution, and then 300 ml of water, and after drying with anhydrous magnesium sulfate, the solvent was distilled off to provide 44 g of methyl 5-acetyl-2-methylbenznesulfinate.

(b). In 200 ml of chloroform was dissolved 21.2 g of methyl 5-acetyl-2-methylbenzenesulfinate and then 16.8 g of bromine was added dropwise to the solution with stirring at 40° C. After the reaction was over, the reaction mixture was added to 500 ml of water and the chloroform layer formed was recovered, washed with a saturated aqueous sodium hydrogen-carbonate solution, and dried with anhydrous magnesium sulfate. Then, the solvent was distilled off and the crude crystals formed were recrystallized from ethanol to provide 26 g of methyl 5-bromoacetyl-2-methylbenzenesulfinate having a melting point of 123°–125° C.

REFERENCE EXAMPLE 3

(a). While ice-cooling a suspension of 84 g of stannous chloride-2H$_2$O in 320 ml of glacial acetic acid with stirring until a transparent solution was obtained, hydrochloric acid gas was introduced into the solution and then 14.3 g of 3-chlorosulfonyl-4-methoxyphenylacetone was added to the solution at 25°–30° C. After further stirring the mixture at room temperature for 30 minutes, the reaction mixture obtained was poured into 320 ml of concentrated hydrochloric acid and after diluting the mixture with 640 ml of water, the product was extracted with 400 ml of chloroform. The chloroform layer formed was washed with water and then chloroform was distilled off to provide 10 g of oily 3-mercapto-4-methoxyphenylacetone.

(b). A mixture of 10 g of 3-mercapto-4-methoxyphenylacetone, 9 g of anhydrous potassium carbonate, 42 g of methyl iodine, and 50 ml of methyl ethyl ketone was stirred under refluxing for 20 hours, and after cooling, the reaction mixture was filtered. The filtrate obtained was, then, evaporated to dryness. The residue formed was dissolved in ethyl acetate and after washing the solution obtained with water, ethyl acetate was distilled off and the crude crystals obtained were recrystallized from a mixture of n-hexane and ether to provide 9 g of 3-methylthio-4-methoxyphenylacetone having a melting point of 74°–75° C.

(c). By following the same procedure as in above process (b) using isopropyl iodide as an alkylating agent, oily 4-isopropylthio-3-methoxyphenylacetone was obtained. The product obtained shows the following nuclear magnetic resonance spectra.

Nuclear magnetic resonance spectra (CDCl$_3$):

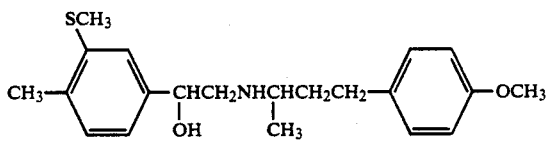

EXAMPLE 1

A mixture of 6 g of 4-methyl-3-methylthiostyrene oxide and 7 g of 3-(4-methoxyphenyl)-1-methylpropylamine was heated to 115° C. for 3 hours. After the reaction was over, the reaction mixture was dissolved in 100 ml of benzene and after washing twice each time with 200 ml of water, the benzene layer was purified by a silica gel column chromatography (eluate: a mixture of benzene, ethyl acetate, and methanol (4:3:1 by volume ratio) to provide 3.5 g of amorphous α-{[3-(4-methoxyphenyl)-1-methylpropylamino]methyl}-4-methyl-3-methylthiobenzenemethanol.

The product has the following physicochemical properties:

(i) Amorphous form (ii) Elemental analysis for C$_{21}$H$_{29}$NO$_2$S:

|  | C (%) | H (%) | N (%) |
|---|---|---|---|
| Calculated: | 70.16 | 8.13 | 3.90 |
| Found: | 69.98 | 8.20 | 3.75 |

(iii) Nuclear magnetic resonance spectra (CDCl$_3$):

δ: 1.50 (3H, d, C$\underline{H}_3$—CH)

2.25 (3H, s, —C$\underline{H}_3$—⟨phenyl⟩)

2.37 (3H, s, C$\underline{H}_3$—S)
3.79 (3H, s, C$\underline{H}_3$—O)
4.70 (1H, m, C$\underline{H}$—OH)

By following almost same procedure as in Example 1, the compounds shown in following Example 2 and Example 3 were obtained.

EXAMPLE 2

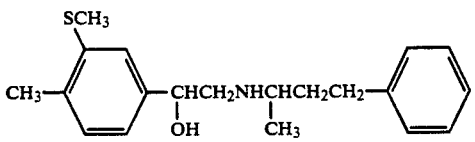

α-{[(1-Methyl-3-phenyl)propylamino]methyl}-4-methyl-3-methylthiobenzenemethanol.
Physicochemical properties:
(i) Melting point: 48°-60° C.
(ii) Elemental analysis for $C_2OH_{27}NOS$:

|  | C (%) | H (%) | N (%) |
|---|---|---|---|
| Calculated: | 72.90 | 8.26 | 4.25 |
| Found: | 72.80 | 8.26 | 4.36 |

(iii) Nuclear magnetic resonance spectra (CDCl$_3$):

δ: 1.10 (3H, d, C$\underline{H}_3$—CH)

2.30 (3H, s, C$\underline{H}_3$—⌬)

2.42 (3H, s, C$\underline{H}_3$—S)
4.61 (1H, q, C$\underline{H}$—OH)

EXAMPLE 3

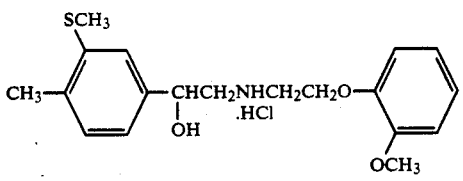

α-{[2-(2-Methoxyphenoxy)ethylamino]methyl}-4-methyl-3-methylthiobenzenemethanol hydrochloride.
Physicochemical properties:
(i) Melting point: 97°-98° C.
(ii) Elemental analysis for $C_{19}H_{25}NO_3S + HCl$:

|  | C (%) | H (%) | N (%) |
|---|---|---|---|
| Calculated: | 59.44 | 6.83 | 3.65 |
| Found: | 59.20 | 6.92 | 3.42 |

(iii) Nuclear magnetic resonance spectra (CDCl$_3$):

δ: 2.26 (3H, s, C$\underline{H}_3$—⌬)

2.37 (3H, s, C$\underline{H}_3$—S)
3.76 (3H, s, C$\underline{H}_3$—O)
4.84 (1H, m, C$\underline{H}$—OH)

EXAMPLE 4

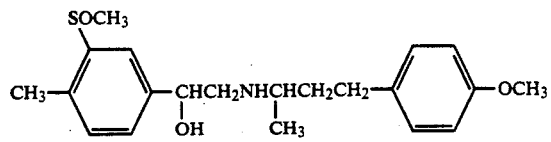

In 70 ml of methanol was dissolved 2.5 g of α-{[3-(4-methoxyphenyl)-1-methylpropylamino]-methyl}-4-methyl-3-methylthiobenzenemethanol and then 8 ml of an aqueous 30% hydrogen peroxide solution was added dropwise to the solution under ice-cooling. After allowing the reaction mixture to stand overnight at room temperature, methanol was distilled off and after adding 50 ml of water to the residue, the product was extracted with ethyl acetate. The ethyl acetate layer formed was dried with anhydrous magnesium sulfate and after distilling off the solvent, the residue was purified by a silica gel column chromatography (eluate: a mixture of benzene, ethyl acetate, and methanol (4:3:1 by volume ratio) to provide 2.0 g of the amorphous caramel-like powder of α-{[3-(4-methoxyphenyl)-1-methylpropylamino]methyl}-4-methyl-3-methylsulfinylbenzenemethanol.

The product has the following physicochemical properties:
(i) Amorphous form
(ii) Elemental analysis for $C_{21}H_{29}NO_3S$:

|  | C (%) | H (%) | N (%) |
|---|---|---|---|
| Calculated: | 67.17 | 7.78 | 3.73 |
| Found: | 67.38 | 7.69 | 3.52 |

(iii) Nuclear magnetic resonance spectra (CDCl$_3$):

δ: 1.04 (3H, d, C$\underline{H}_3$—CH)

2.46 (3H, s, C$\underline{H}_3$—⌬)

2.79 (3H, s, C$\underline{H}_3$—SO)
3.73 (3H, s, C$\underline{H}_3$—O)
4.58 (1H, q, C$\underline{H}$—OH)

By following substantially the same procedure as in Example 4, the compound shown in the following Example 5 was obtained.

EXAMPLE 5

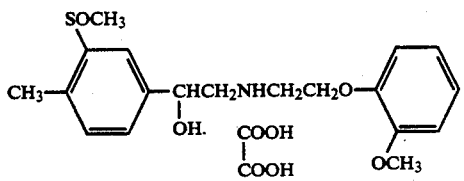

α-{[2-(2-Methoxyphenoxy)ethylamino]methyl}-4-methyl-3-methylsulfinylbenzenemethanol oxalate.
Physicochemical properties:
(i) Melting point: 182°-184° C.
(ii) Elemental analysis for $C_{19}H_{25}NO_4S + (COOH)_2$:

|  | C (%) | H (%) | N (%) |
| --- | --- | --- | --- |
| Calculated: | 55.62 | 6.00 | 3.09 |
| Found: | 55.49 | 5.95 | 3.16 |

(iii) Nuclear magnetic resonance spectra (CDCl₃)

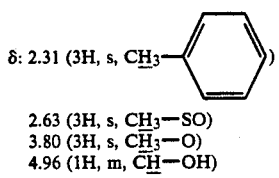

δ: 2.31 (3H, s, C$\underline{H}$₃—⬡)
2.63 (3H, s, C$\underline{H}$₃—SO)
3.80 (3H, s, C$\underline{H}$₃—O)
4.96 (1H, m, C$\underline{H}$—OH)

EXAMPLE 6

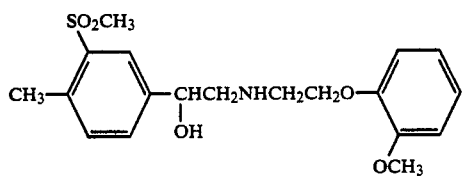

A mixture of 5.8 g of methyl 5-bromoacetyl-2-methylbenzenesulfinate, 160 ml of methyl ethyl ketone, and 10.3 g of N-benzyl-2-(o-methoxyphenoxy)ethylamine was refluxed with stirring for 40 minutes. After the reaction was over, the solvent was distilled off, 150 ml of ethyl acetate was added to the residue formed, and N-benzyl-2-(2-methoxyphenoxy)ethylamine hydrobromide precipitated was removed by filtration. The solvent was distilled off from the filtrate, the residue obtained was dissolved in 125 ml of methanol, and 1.5 g of sodium borohydide was added to the solution under ice-cooling.

The mixture was stirred for 2 hours at room temperature and then methanol was distilled off. After adding 100 ml of water to the residue formed, the product was extracted with 200 ml of ethyl acetate, the ethyl acetate layer obtained was washed with water, and after drying by anhydrous magnesium sulfate, the solvent was distilled off to provide 10 g of oily α-{2-[N-benzyl-2-(2-methoxyphenoxy)ethylamino]methyl}-4-methyl-3-methoxysulfinylbenzenemethanol. The product was dissolved in 100 ml of methanol and after adding 0.8 g of 10% palladium carbon, the product was subjected to catalytic reduction at normal temperature and normal pressure. After the reaction was over, palladium carbon was removed by filtration and the filtrate was evaporated to dryness. To the residue obtained was added a solution of 1.7 g of oxalic acid dissolved in 17 ml of methanol and the mixture was allowed to stand overnight at room temperature to provide 6 g of colorless crystals. The crystals were recrystallized from 30 ml of methanol to provide α-{[2-(2-methoxyphenoxy)ethylamino]methyl}-4-methyl-3-methoxysulfinylbenzenemethanol oxalate.

The product has the following physicochemical properties:

Melting point: 185°–188° C.
Elemental analysis for C₁₉H₂₅NO₅S+(COOH)₂:

|  | C (%) | H (%) | N (%) |
| --- | --- | --- | --- |
| Calculated: | 53.72 | 5.80 | 2.98 |
| Found: | 53.62 | 5.76 | 3.09 |

Nuclear magnetic resonance spectra (d₆-DMSO):

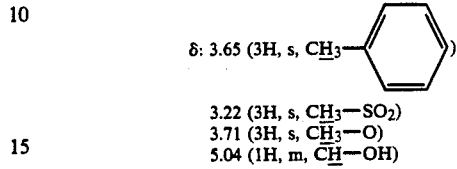

δ: 3.65 (3H, s, C$\underline{H}$₃—⬡)
3.22 (3H, s, C$\underline{H}$₃—SO₂)
3.71 (3H, s, C$\underline{H}$₃—O)
5.04 (1H, m, C$\underline{H}$—OH)

EXAMPLE 7

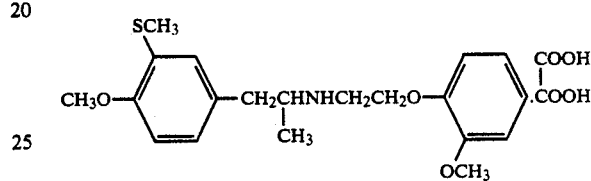

A mixture of 8.4 g of 4-methoxy-3-methylthiophenylacetone, 6.7 g of 2-methoxyphenoxyethylamine, and 150 ml of methanol was refluxed for 2 hours. The reaction mixture was cooled to a temperature below 10° C. and after adding 2.5 g of sodium borohydride to the reaction mixture with stirring at temperatures below 10° C., the mixture was further stirred for 3 hours at room temperature. Then, the solvent was distilled off under reduced pressure and after adding water to the residue, the product was extracted with ethyl acetate. The extract was washed with water, dried by anhydrous magnesium sulfate, and then the solvent was distilled off to provide an oily product. The product was purified by a silica gel column chromatography (eluate: chloroform) to provide 8.5 g of 4-{2-[2-(2-methoxyphenoxy)ethylamino]-2-methylethyl}-2-(methylthio)anisole. The product (750 mg) was dissolved in 10 ml of methanol and after adding thereto a solution of 90 mg of anhydrous oxalic acid dissolved in 1 ml of methanol, the mixture was allowed to stand overnight at room temperature. The crystals thus formed were recovered by filtration and recrystallized from ethanol to provide 600 mg of 4-{2-[2-(2-methoxyphenoxy)ethylamino]-2-methylethyl}-2-(methylthio)anisole oxalate having a melting point of 173°–174° C.

Physicochemical properties:
(i) Elemental analysis for C₂₀H₂₇NO₃S+(COOH)₂:

|  | C (%) | H (%) | N (%) |
| --- | --- | --- | --- |
| Calculated: | 58.52 | 6.47 | 3.10 |
| Found: | 58.33 | 5.93 | 2.97 |

(ii) Nuclear magnetic resonance spectra (CDCl₃):
δ:1.08 (3H, d, C$\underline{H}$₃—CH); 2.38 (3H, s, C$\underline{H}$₃S—); 3.78 (3H, s, C$\underline{H}$₃—O—); 3.86 (3H, s, C$\underline{H}$₃—O—).

By following substantially the same procedure as in Example 7, the compound shown in following Example 8 was obtained.

EXAMPLE 8

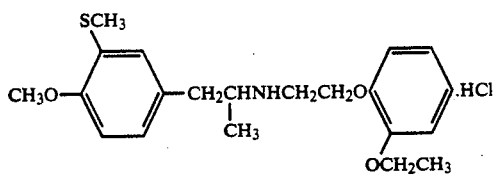

4-{2-[2-(2-Ethoxyphenoxy)ethylamino]-2-methylethyl}-2-(methylthio)anisole hydrochloride.

Physicochemical properties:
(i) Melting point: 88°–89° C.
(ii) Elemental analysis for $C_{21}H_{29}NO_3S + HCl + \frac{1}{4} H_2O$

|  | C (%) | H (%) | N (%) |
| --- | --- | --- | --- |
| Calculated: | 59.91 | 7.42 | 3.33 |
| Found: | 59.74 | 7.45 | 3.45 |

(iii) Nuclear magnetic resonance spectra (CDCl$_3$); δ: 2.31 (3H, s, CH$_3$—S); 3.84 (3H, s, CH$_3$—O); 4.44 (2H, t, CH$_2$—O).

EXAMPLE 9

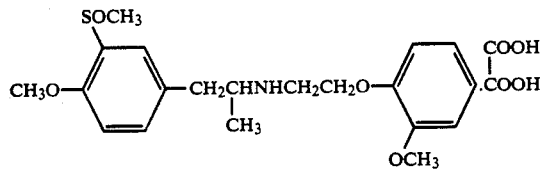

In 100 ml of a mixture of methanol and water (5:1) was dissolved 1.8 g of 4-{2-[2-(2-methoxyphenoxy)ethylamino]-2-methylethyl}-2-(methylthio)anisole and after adding dropwise thereto 10.5 ml of an aqueous solution of 0.5M sodium metaperoiodate at 0° C., the mixture was stirred overnight at 4° C. The crystals formed were removed by filtration and the filtrate was concentrated under reduced pressure and the residue formed was purified by a silica gel column chromatography (eluate: a mixture of chloroform and methanol (97:3 by volume ratio) to provide 722 mg of oily 4-{2-[2-(2-methoxyphenoxy)ethylamino]-2-methylethyl}-2-(methylsulfinyl)anisole. The product was dissolved in 10 ml of methanol and after adding thereto a solution of 252 mg of oxalic acid di-hydrate dissolved in 6 ml of methanol, the mixture was allowed to stand overnight at room temperature. The resulting crystalline material was recovered by filtration and recrystallized from ethanol to provide 700 mg of 4-{2-[2-(2-methoxyphenoxy)ethylamino]-2-methylethyl}-2-(methylsulfinyl)anisole oxalate having a melting point of 172°–174° C. The product has the following physicochemical properties:

(i) Elemental analysis for $C_{20}H_{27}NO_4S + (COOH)_2$:

|  | C (%) | H (%) | N (%) |
| --- | --- | --- | --- |
| Calculated: | 56.52 | 6.25 | 3.00 |
| Found: | 56.17 | 6.25 | 3.01 |

(ii) Nuclear magnetic resonance spectra (d$_6$-DMSO): δ:1.12 (3H, d, CH$_3$—CH); 2.68 (3H, s, CH$_3$SO—); 3.76 (3H, s, CH$_3$—O—); 3.84 (3H, s, CH$_3$—O—).

EXAMPLE 10

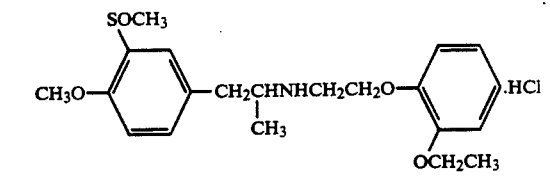

In 30 ml of ethanol was dissolved 1.0 g of 4-{2-[2-(2-ethoxyphenoxy)ethylamino]-2-methylethyl}-2-(methylthio)anisole hydrochloride and then 0.5 g of an aqueous 35% hydrogen peroxide solution was added to the solution with stirring. After stirring the mixture for 18 hours at room temperature, ethanol was distilled off under reduced pressure and the remaining sticky product was dispersed in 20 ml of water and extracted with 100 ml of ethyl acetate. The ethyl acetate layer was washed three times each time each with 20 ml of water and after acidifying the solution with 0.2 ml of concentrated hydrochloric acid, the solvent was distilled off under reduced pressure. The remaining sticky material was applied to a silica gel column chromatography and eluted using a mixture of ethyl acetate and methanol (4:1 by volume ratio). The sticky product obtained was crystallized by the addition of 3 ml of isopropanol and the crystals thus formed were recovered by filtration to provide 0.4 g of 4-{2-[2-(2-ethoxyphenoxy)ethylamino]-2-methylethyl}-2-(methylsulfinyl)anisole hydrochloride.

The product has the following physicochemical properties:
(i) Melting point: 154°–160° C.
(ii) Elemental analysis for $C_{21}H_{29}NO_4S + HCl$:

|  | C (%) | H (%) | N (%) |
| --- | --- | --- | --- |
| Calculated: | 58.93 | 7.06 | 3.27 |
| Found: | 58.64 | 7.07 | 3.41 |

(iii) Nuclear magnetic resonance spectra (CDCl$_3$): δ:2.70 (3H, s, CH$_3$—SO); 3.82 (3H, s, CH$_3$—O); 4.43 (3H, t, CH$_2$—O).

EXAMPLE 12

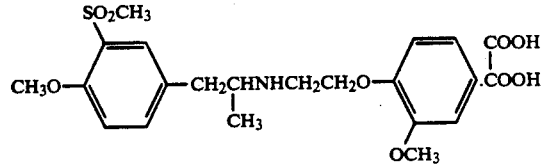

In 18 ml of glacial acetic acid was dissolved 1.8 g of 4-{2-[2-(2-methoxyphenoxy)ethylamino]-2-methylethyl}-2-(methylthio)anisole and then 1.15 g of an aqueous 30% hydrogen peroxide solution was added dropwise to the solution under ice-cooling. After heating the mixture to 60° C. for one hour, 100 ml of water was added to the reaction mixture and the product was extracted with ethyl acetate. The ethyl acetate layer was washed with water, dried with anhydrous magnesium sulfate, and then the solvent was distilled off. The residue obtained was purified by a silica gel column chromatography (eluate: a mixture of chloroform and methanol (97:3 by volume ratio) to provide 1 g of oily 4-{2-[2-(2-methoxyphenoxy)ethylamino]-2-methylethyl}-2-(methylsulfonyl)anisole. The product was dissolved in 10 ml of methanol and after adding thereto a solution of 230 mg of anhydrous oxalic acid dissolved in 2 ml of methanol, the mixture was allowed to stand overnight at room temperature. The crystals thus formed were recovered by filtration and recrystallized from methanol to provide 700 mg of 4-{2-[2-(2-methoxyphenoxy)ethylamino]-2-methylethyl}-2-(methylsulfonyl)anisole oxalate having a melting point of 194°–195° C.

The product has the following physicochemical properties:

(i) Elemental analysis for $C_{20}H_{27}NO_5S + (COOH)_2$:

|  | C (%) | H (%) | N (%) |
|---|---|---|---|
| Calculated: | 54.65 | 6.04 | 2.90 |
| Found: | 54.48 | 6.06 | 3.09 |

(ii) Nuclear magnetic resonance spectra (d$_6$-DMSO):
δ:1.12 (3H, d, C$\underline{H}_3$—CH); 3.16 (3H, s, C$\underline{H}_3$—SO$_2$—); 3.72 (3H, s, C$\underline{H}_3$—O—); 3.92 (3H, s, C$\underline{H}_3$—O—).

By following substantially the same procedure as in Example 11, the compounds shown in the following examples were obtained.

EXAMPLE 12

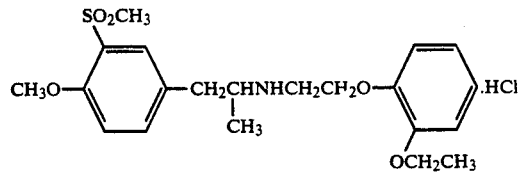

4-{2-[2-(2-Ethoxyphenoxy)ethylamino]-2-methylethyl}-2-(methylsulfonyl)anisole hydrochloride.
Physicochemical properties:
(i) Melting point: 193°–196° C.
(ii) Elemental analysis for $C_{21}H_{29}NO_5S + HCl$:

|  | C (%) | H (%) | N (%) |
|---|---|---|---|
| Calculated: | 56.81 | 6.81 | 3.15 |
| Found: | 56.53 | 6.82 | 3.23 |

(iii) Nuclear magnetic resonance spectra (CDCl$_3$):
δ:3.16 (3H, s, C$\underline{H}_3$—SO$_2$); 3.94 (3H, s, C$\underline{H}_3$—O); 4.44 (2H, t, C$\underline{H}_2$—O).

EXAMPLE 13

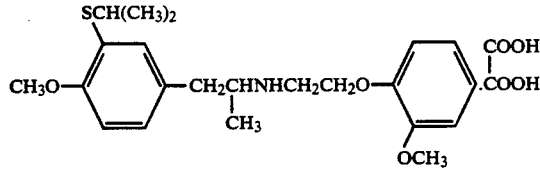

4-{2-[2-(2-Methoxyphenoxy)ethylamino]-2-methylethyl}-2-(isopropylthio)anisole oxalate.
Physicochemical properties:
(i) Melting point: 157°–158° C.

(ii) Elemental analysis for $C_{22}H_{31}NO_3S + (COOH)_2$:

|  | C (%) | H (%) | N (%) |
|---|---|---|---|
| Calculated: | 60.11 | 6.94 | 2.92 |
| Found: | 60.10 | 7.05 | 2.84 |

(iii) Nuclear magnetic resonance spectra (d$_6$-DMSO):

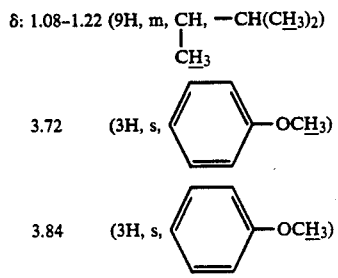

EXAMPLE 14

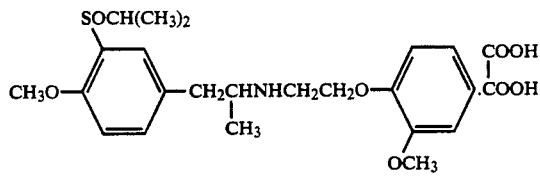

4-{2-[2-(2-Methoxyphenoxy)ethylamino]-2-methylethyl}-2-(isopropylsulfinyl)anisole oxalate.
Physicochemical properties:
(i) Melting point: 146°–147° C.
(ii) Elemental analysis for $C_{22}H_{31}NO_4S + (COOH)_2$:

|  | C (%) | H (%) | N (%) |
|---|---|---|---|
| Calculated: | 58.17 | 6.71 | 2.83 |
| Found: | 58.17 | 6.73 | 2.94 |

(iii) Nuclear magnetic resonance spectra (d$_6$-DMSO):

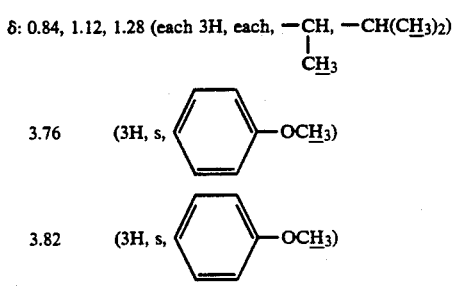

EXAMPLE 15

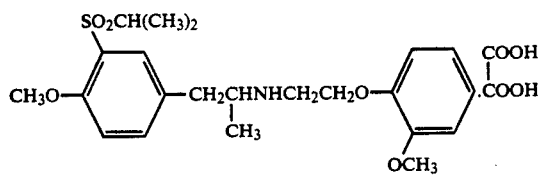

4-{2-[2-(2-Methoxyphenoxy)ethylamino]-2-methylethyl}-2-(isopropylsulfonyl)anisole oxalate.

Physicochemical properties:
(i) Melting point: 200°–202° C.
(ii) Elemental analysis for $C_{22}H_{31}NO_5S+(COOH)_2$:

|  | C (%) | H (%) | N (%) |
|---|---|---|---|
| Calculated: | 56.35 | 6.50 | 2.74 |
| Found: | 56.60 | 6.43 | 2.68 |

(iii) Nuclear magnetic resonance spectra ($d_6$-DMSO):

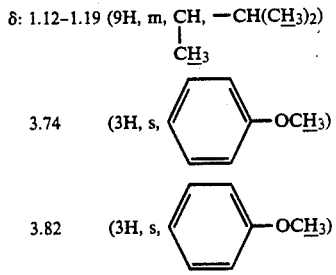

The compounds of this invention can be administered orally or parenterally but intranenous injection or oral administration is preferred. The compounds of this invention are used as the free bases or the pharmacologically acceptable salts thereof and, in general, they are used as medical or pharmaceutical compositions with carriers or diluents which can be used generally for preparing medicaments.

In the case of oral administration, it is most convenient to use the medical compositions of this invention in the form of capsules or tablets but they may also be used as a sustained release preparation. Furthermore, the compositions may be used as sugarcoated preparations or syrups. The doses thereof at oral administration depend on the kind of disease, the age of the patient, etc. Generally, it is proper to administer 0.005–0.03 mg per single dose of the compound several times per day in case of intravenous administration or 200–2000 mg of the compound in two or three times per day case of oral administration.

EXAMPLE A

Medical composition—tablet for oral administration.
Formulation for 1,000 tablets:

| Active component | 100 g |
|---|---|
| Starch | 185 g |
| Milk sugar | 25 g |
| Magnesium stearate | 1.5 g |

The components shown above were granulated in an ordinary manner using starch pase as a binder and then molded into tablets each having a 9.5 mm diameter.

What we claim is:

1. A phenethylamine derivative of the formula

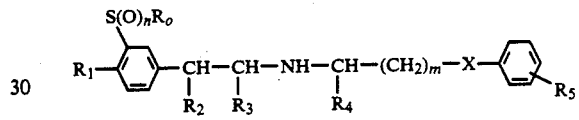

wherein $R_0$ represents a lower alkyl group; $R_1$ represents a lower alkyl group or a lower alkoxy group; $R_2$ represents a hydrogen atom; $R_3$ represents a hydrogen atom or a lower alkyl group; $R_4$ represents a hydrogen atom, $R_5$ represents a hydrogen atom or a lower alkoxy group: X represents an oxygen atom; m is an integer of 1; and n is an integer of 2 and the pharmacologically acceptable acid addition salts thereof.

2. The Phenethylamine derivative which is 4-{2-[2-(2-ethoxyphenoxy)ethylamino]-2-methylethyl}-2-(methylsulfonyl)anisole.

3. The Phenethylamine derivative which is 4-{2-[2-(2-ethoxyphenoxy)ethylamino]-2-methylethyl}-2-(methylthio)-anisole.

* * * * *